(12) United States Patent
Schouwink et al.

(10) Patent No.: US 9,121,996 B2
(45) Date of Patent: Sep. 1, 2015

(54) OBJECTIVE OF AN ANGULARLY VIEWING, RIGID ENDOSCOPE

(75) Inventors: Peter Schouwink, Hamburg (DE); Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 288 days.

(21) Appl. No.: 13/810,179

(22) PCT Filed: Jul. 7, 2011

(86) PCT No.: PCT/EP2011/003373
§ 371 (c)(1),
(2), (4) Date: Mar. 27, 2013

(87) PCT Pub. No.: WO2012/007126
PCT Pub. Date: Jan. 19, 2012

(65) Prior Publication Data
US 2013/0176638 A1    Jul. 11, 2013

(30) Foreign Application Priority Data
Jul. 13, 2010   (DE) .......................... 10 2010 027 079

(51) Int. Cl.
| G02B 5/04 | (2006.01) |
| A61B 1/00 | (2006.01) |
| G02B 13/00 | (2006.01) |
| G02B 23/24 | (2006.01) |
| G02B 5/00 | (2006.01) |

(52) U.S. Cl.
CPC .............. *G02B 5/04* (2013.01); *A61B 1/00179* (2013.01); *G02B 13/0065* (2013.01); *G02B 23/243* (2013.01); *G02B 5/003* (2013.01)

(58) Field of Classification Search
None
See application file for complete search history.

(56) References Cited

FOREIGN PATENT DOCUMENTS

| DE | 35 37 155 C2 | 3/1988 |
| DE | 36 40 186 | 6/1988 |
| DE | 19720 163 | 11/1997 |
| EP | 0 571 725 | 12/1993 |
| JP | 2-108013 | 4/1990 |

OTHER PUBLICATIONS

International Search Report dated Sep. 1, 2011 issued in PCT/EP2011/003373.
International Preliminary Report on Patentability PCT/EP2011/003373, together with the Written Opinion dated Jan. 24, 2013.

*Primary Examiner* — Jade R Chwasz
(74) *Attorney, Agent, or Firm* — Scully, Scott, Murphy & Presser, P.C.

(57) ABSTRACT

An objective of an oblique viewing, rigid endoscope, including a prism arrangement consisting of distal and proximal prisms contacting with planar contact surfaces that are oblique to an axis of the objective, the distal prism includes a distal front face toward the viewing direction of the objective, from which the rays entering there enter through the distal prism and through a passage area of the contact surfaces into the proximal prism and after double reflection in the proximal prism on a first mirror on a diagonal surface and a second mirror on the contact surface exit in the direction of the axis of the objective through a surface perpendicular to the direction of the axis of the objective, wherein the second mirror is arranged outside the penetration area, and an absorption layer is arranged in the plane of the second mirror between this and the penetration area.

3 Claims, 1 Drawing Sheet

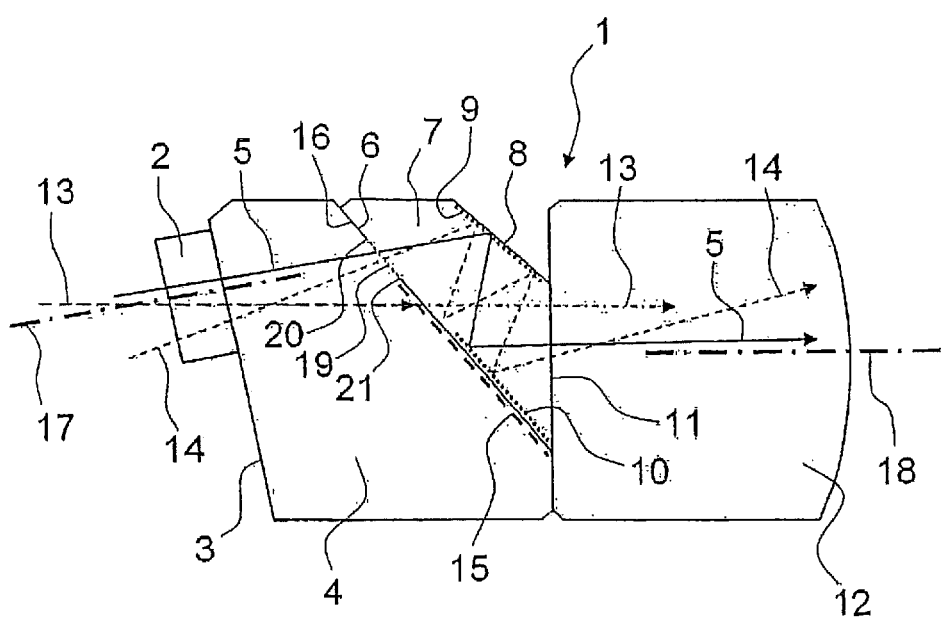

OBJECTIVE OF AN ANGULARLY VIEWING, RIGID ENDOSCOPE

CROSS-REFERENCE TO RELATED APPLICATION

The present application is based upon and claims the benefit of priority from PCT/EP2011/003373 filed on Jul. 7, 2011, which claims benefit to DE 10 2010 027 079.2 filed on Jul. 13, 2010, the entire contents of each of which are incorporated herein by reference.

BACKGROUND

1. Field

The present invention generally relates to an objective of an angularly viewing, rigid endoscope, and particularly to an objective of the type referred to in claim 1.

2. Prior Art

Objectives of endoscopes have a number of problems, such as that endoscopes should usually be very thin which results in the fact that the objectives must have fewer millimeters in the diameter area. Rigid objectives also have the problem that they must be usually shaped angularly viewing, wherein the viewing direction of the objective is at an angle to the axis of the objective, in which the ray are emitted in a proximal direction through the main part of the objective, for example, directly onto an image receiver or an image guide conducting the image over the length of the endoscope. The change of direction of the beams between these two directions usually occurs by a prism arrangement.

DE 197 20 163 A1, FIG. 3 shows a generic objective, wherein the prism arrangement is comprised of two prisms, of which the proximal prism emits the rays after two reflections on mirrors in the direction of the axis of the objective. DE 35 37 155 C2 shows a similar design with an absorption layer.

So far unsolved problems occur on the second mirror. The second mirror must be limited in the direction of the passage area of the rays through the contact area, because it would otherwise partially interrupt the rays. However, if the second mirror does not protrude far enough in the direction of passage area, rays entering angularly with respect to the viewing direction can go past the second mirror and also the first mirror directly through the proximal prism into the proximal direction towards the viewer and generate disturbing effects there. For this reason, the second mirror must come as close as possible to the passage area. However, another effect will then interfere. Oblique rays which pass very inclined through the contact surfaces can be so inclined in the proximal prism between the mirrors that they again run back and forth, and are therefore reflected a total of four times. This also results in disturbances. The problem of the quadruple reflection is all the stronger, the smaller the slanted viewing angle is. The designer here is therefore at a dilemma between two interfering effects that occur at an either too long or too short mirror. An average length is also unsatisfactory because both effects can then occur.

SUMMARY

An object of the present invention consists in avoiding the problems that result in a generic objective from the length of the second mirror.

According to the invention, an absorption layer is provided in the area adjacent to the passageway area in which the second mirror is missing and a ray could therefore pass directly past both mirrors, that the absorption layer could absorb a ray running straight through the objective. However, the absorption layer also prevents the quadruple reflection in the proximal prism, since in the case of steep rays these impact the absorption layer after the first reflection and are absorbed there. In this very simple design, both interfering effects are simultaneously counteracted.

The absorption layer could be arranged adjacent to the second mirror, however, is preferably, according to claim 2, overlapping. Since the mirror must reflect towards the proximal prism, it can only be arranged on the outer side of the mirror facing the distal prism. There, the absorption layer does not interfere, but rather acts advantageous in that it prevents internal reflections on this mirror in the distal prism.

The mirror and the overlapping absorption layer could both be superposed on the contact surface of the distal prism or that of the proximal prism. However, advantageously according to claim 3, the mirror is arranged on the distal prism and the absorption layer on the proximal prism, which allows an easy production.

BRIEF DESCRIPTION OF THE DRAWING

In the drawing, the invention is shown schematically, for example, in the FIGURE, which shows an axial section through the distal part of an inventive objective of a rigid endoscope.

Referring to FIGS. 1 to 3 of DE 197 20 163 A1. When comparing FIGS. 2 and 3 of this document, it becomes clear that the objective part of the objective shown in the FIGURE of the present application is the distal end region of the known design.

In the very schematically shown area of objective 1, the light enters through a negative objective array 2, which is mounted on the distal front face 3 of a distal prism 4. A centre image ray 5 runs parallel to viewing direction 17 of objective 1 through the negative objective arrangement 2, through distal prism 4 and into a proximal prism 7 located behind Image ray 5 thereby penetrates a contact surface 6 of prism 4 and a contact surface 16 of prism 7. Prisms 4, 7 contact with these plane contact surfaces 6, 16.

Ray 5 then meets a diagonal surface 8 of the proximal prism 7, which is provided with a inward first reflective mirror 9, which is shown as a dotted line. After the reflection there, ray 5 meets a second mirror 10, which is also shown as a dotted line and which is arranged on the contact surface of proximal prism 7. From there, ray 5 is further reflected in proximal direction toward the viewer. In the illustrated example, ray 5 is now in axis 18 of the objective and falls through a transverse surface 11, which is perpendicular to axis 18 of the objective into an objective 12, from which it extends further into the proximal part of the objective, which is not shown, and is indicated in FIG. 3 of the document mentioned with reference numeral 35.

As the FIGURE shows, the distal front face 3 of the distal prism 4 is perpendicular to viewing direction 17 of the objective, which is at an angle to its axis 18. This is an objective with a very small angular viewing angle.

In as much as previously described, the design shown in the FIGURE is consistent with that of FIG. 3 of the cited document. Two interfering problems can occur here. An oblique ray 13 entering parallel to the axis of the objective can go past the upper end of the second mirror 10 and the lower end of the first mirror 9 straight through proximal prism 7 up to the viewer. This results in strong interferences.

When extending mirror 10 in the direction of the passage area of the rays through contact surfaces 6, 16, then a second interfering effect will occur.

Another oblique ray 14, which is located in the other direction so that it impacts more inclined on the first mirror 9, is reflected so at a narrow angle of reflection that it is not reflected twice as the regular ray 5, therefore once on the first mirror 9 and once on the second mirror 10, but runs once more back and forth, so that it is reflected four times in total, as illustrated by ray 14.

If mirror 10 is as short as shown in the FIGURE, as the FIGURE shows, this quadruple reflection cannot occur. But if it is extended to prevent the penetration of ray 13, then the quadruple reflection of ray 14 occurs.

In order to prevent ray 13, mirror 10 would therefore have to be extended. In order to prevent the quadruple reflection of ray 14, it would have to be shortened again. A design dilemma exists.

A surface area of contact surfaces 6, 16 is marked in dashed lines in the FIGURE as penetration area 19. Penetration area 19 extends in the illustration of the FIGURE, between points 20 and 21. Penetration area 19 is penetrated by rays duly passing through the objective.

The surface area of the contact surfaces 6, 16, which is adjacent to the penetration area 19 beyond point 21, is critical both for rays passing straight through without reflection, such as ray 13, as well as for quadruple reflected rays, such as ray 14. According to the invention, an absorption layer 15 represented as a dashed line is provided there. As can be seen in the FIGURE, this absorbs ray 13, but also the interferingly close reflected ray 14. Absorbing layer 15 can readily extend close to penetration area 19 and therefore obstruct the directly penetrating ray 13 and the quadruple reflected ray 14 in a broad range of angles.

Absorption layer 15 must not extend into penetration area 19, since it would there absorb usable rays, however, it should always cover the critical surface between penetration area 19 and the second mirror 10. As illustrated, however, absorption layer 15 may also be arranged to overlap mirror 10, and therefore cover the same surface of contact surfaces 6, 16 parallel to that.

Mirror 9 is arranged as a metal coating on the outside of the diagonal surface 8 of proximal prism 7. Similarly, the second mirror 10 is mounted on its contact surface 16 from the outside. The absorption layer 15 is arranged on contact surface 6 of prism 4 and consists, for example, of black chrome.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An objective lens of an angularly viewing, rigid endoscope, the objective lens comprising:
    a prism arrangement comprising distal and proximal prisms, both contacting with planar contact surfaces that are inclined relative to an axis,
    the distal prism includes a distal end face positioned perpendicular to a viewing direction, from which a ray incident on the distal end face along the viewing direction is transmitted through the distal prism and through a penetration area of the planar contact surfaces and into the proximal prism, in which the ray is reflected at a first angle by a first mirror disposed on an inclined surface facing the planar contact surfaces, the ray is then reflected by a second mirror disposed on one of the contact surfaces and is emitted through a surface that is perpendicular to the axis and along a direction of the axis,
    wherein
    the contact surfaces are inclined to the distal end face;
    the second mirror is spaced apart from the penetration area in an inclining direction of the contact surfaces,
    an absorption layer is provided in the contact surfaces;
    the absorption layer is positioned between a region at which the second mirror is disposed and the penetration area; and
    an oblique ray, that is incident on the distal end face at a predetermined angle relative to the viewing direction, is transmitted through the penetration area, and is reflected by the first mirror at a second angle that is different from the first angle, and is absorbed by the absorption layer.

2. The objective lens according to claim 1, wherein the absorption layer overlaps the second mirror.

3. The objective lens according to claim 2, wherein the second mirror is arranged as a coating on the contact surface of the proximal prism and the absorption layer on the contact surface of the distal prism.

* * * * *